US00PP12597P2

(12) United States Plant Patent
Noodelijk

(10) Patent No.: US PP12,597 P2
(45) Date of Patent: Apr. 30, 2002

(54) CHRYSANTHEMUM PLANT NAMED 'THOR'

(75) Inventor: Robert Noodelijk, Woubrugge (NL)

(73) Assignee: Chrysanthemum Breeders Assoc. N.V. (NL)

( * ) Notice: Subject to any disclaimer, the term of this patent is extended or adjusted under 35 U.S.C. 154(b) by 0 days.

(21) Appl. No.: 09/562,279

(22) Filed: May 1, 2000

(51) Int. Cl.[7] ..... A01H 5/00
(52) U.S. Cl. ..... Plt./290
(58) Field of Search ..... Plt./290

*Primary Examiner*—Bruce R. Campell
*Assistant Examiner*—Annette H. Para
(74) *Attorney, Agent, or Firm*—Parkhurst & Wendel, L.L.P.

(57) ABSTRACT

A chrysanthemum plant named 'THOR' characterized by its large sized blooms with orange ray florets and prolific branching; natural season flower date 5–8 September; blooming for a period of 6 weeks.

2 Drawing Sheets

BACKGROUND OF THE INVENTION

'THOR' is a product of a breeding and selection program for outdoor pot mums (garden mums) which had the objective of creating new chrysanthemum cultivars with a decorative type flower, a natural season flower date around 5–8 September ; blooming for a period of 6 weeks. The new plant of the present invention comprises a new and distinct cultivar of Chrysanthemum plant 'THOR' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in September 1996. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
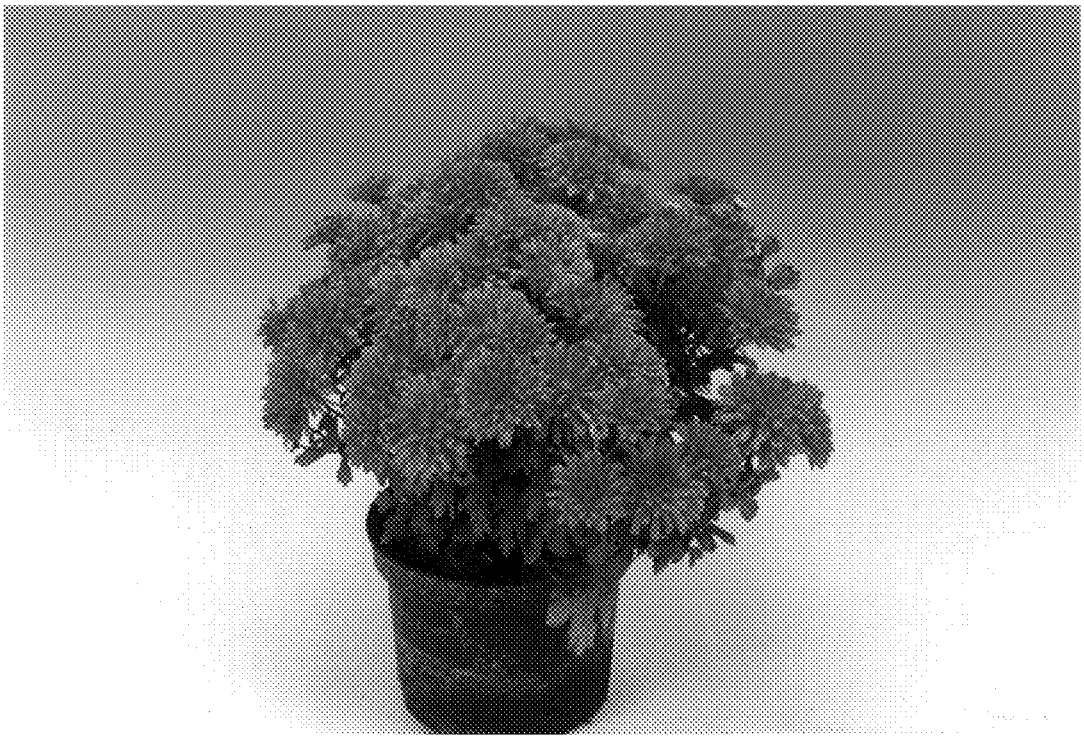
FIG. 1 shows a plant of the cultivar in full bloom.
Figure 2:
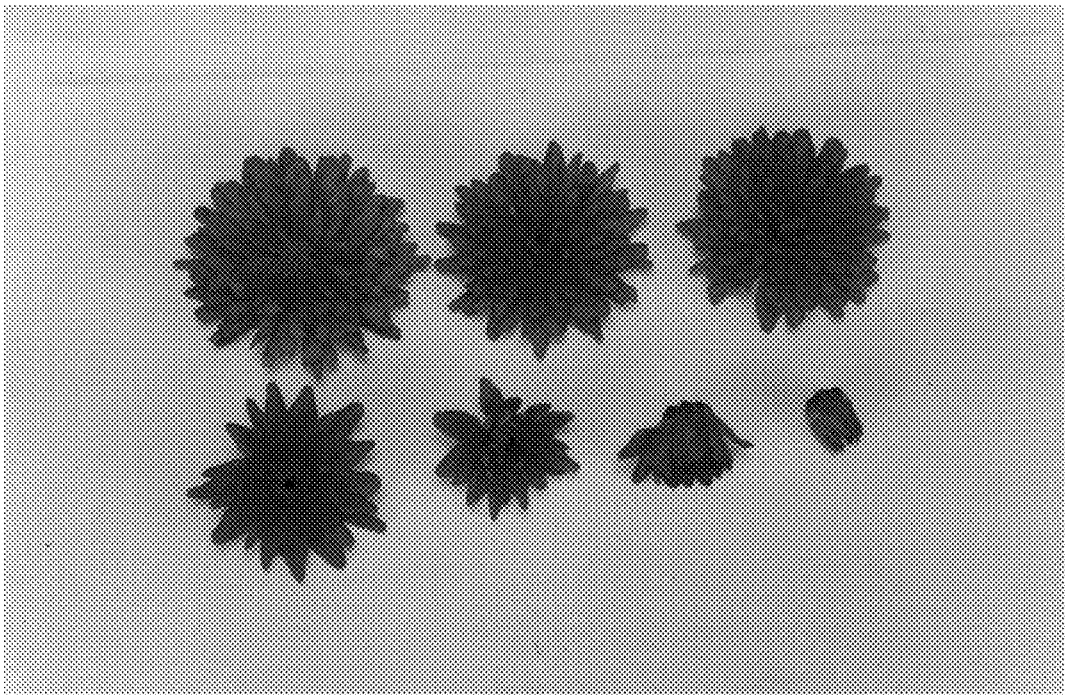
FIG. 2 shows the various stages of bloom of the new cultivar.
Figure 3:
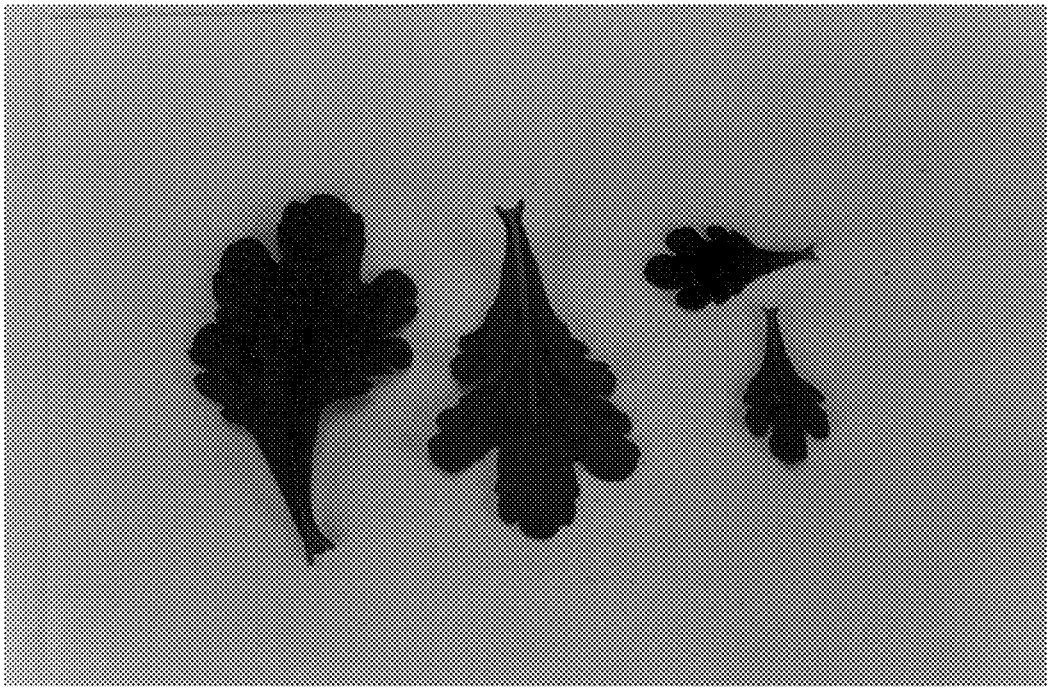
FIG. 3 shows the various stages of foliage and petiole of the new cultivar.

This new variety of chrysanthemum is of the botanical classification *Dendranthema grandiflora*. The observations and measurements were gathered from plants grown out door in Rijsenhout, Holland under natural day length and temperature and planted week 22 in 1997 and 1998. The natural blooming date of this drop was 5–8 September (week 36). The plants were observed (directly) during the flowering of this crop. The average height of the plants was 30–33 cms. No growth retardants were used. No tests were done on cold or drought tolerance. This new variety produces large sized blooms with orange ray florets and orange-yellow disc florets (when visible in a very mature stage)

From the cultivars known to inventor the most similar existing cultivar in comparison to 'THOR' is 'WARM MEGAN' (U.S. Plant Pat. No. 9,126). When 'WARM MEGAN' and 'THOR' are being compared the following differences are noticed: The differences of 'WARM MEGAN' and 'THOR' are (1) Natural flowering date. 'THOR' flowers earlier. (2) Flower color. 'THOR' is a more orange and less bronze. (3) Flower size. 'THOR' has bigger flowers.

The following is a description of the plant and characteristics that distinguish 'THOR' as a new and distinct variety.

The color designations are taken from the 14 week plant itself. Accordingly, any discrepancies between the color designations and the colors depicted in the photographs are due to photographic tolerances. The color chart used in this description is: The Royal Horticultural Society Colour Chart, edition 1995.

Botanical Classification

*Dendranthema grandiflora* 'THOR'

Bud:
- *Size*.—Medium, cross-section 1.4 cm height 1.5 cm.
- *Outside color*.—Orange 26 B.
- *Involucral bracts*.—2 rows, length 7 mm, width 3 mm.
- *Involucral bracts among disc-florets*.—Not present.
- *Involucral bracts color*.—Green 138 A.

Bloom:
- *Type*.—Decorative.
- *Height*.—Medium.
- *Size*.—Large.
- *Fully expanded*.—6.0–6.5 cm.
- *Number of blooms per branch*.—Approx. 4–6 blooms per branch.
- *Performance* (*on the plant*).—6 weeks.
- *Seeds*.—Not produced.
- *Fragrance*.—Typical chrysanthemum.

Color:
- *Center of flower*.—Immature greyed-orange 169 B Mature greyed-orange 169 C the disc orange 25 B.
- *Color of the upper surface of the ray-florets*.—Greyed-orange 169 B.
- *Color of the lower surface of the ray-florets*.—Orange 26 B.

*Tonality from distance*.—A decorative garden mum with orange flowers.
*Discoloration to color*.—Greyed-orange 169 C.

Ray florets:
*Texture*.—Upper side and under side smooth.
*Number*.—180–200.
*Cross-section*.—Convex.
*Longitudinal axis of the majority*.—Straight, outer row reflexing.
*Length of corolla tube*.—Short.
*Ray-floret margin*.—Entire.
*Ray-floret length*.—3.0–3.3 cm.
*Ray-floret width*.—0.4–0.6 cm.
*Ratio length/width*.—High.
*Shape of tip*.—Rounded.

Disc florets:
*Disc diameter*.—0.5 cm.
*Distribution of disc florets*.—Numerous, visible at later stages of flowering.
*Shape*.—Tubular.
*Color*.—Greyed-orange 169 C.
*Receptacle shape*.—Conical raised.

Reproductive organs:
*Stamen* (*present in disc florets only*).—None.
*Pollen*.—None.
*Styles*.—Thin.
*Style color*.—Yellow-green 144 B.
*Style length*.—4 mm.
*Stigmas*.—Yellow-orange 23 A.
*Stigma width*.—1 mm.
*Ovaries*.—Enclosed in calyx.

Plant:
*Type*.—A garden mum (pot mum) meant for out door use.
*Growth habit*.—Spreading.
*Growth rate*.—Rapid.
*Height*.—30–33 cm.
*Width*.—32–35 cm.
*Stem color*.—Green 138 A.
*Stem strength*.—Strong.
*Stem brittleness*.—Present.
*Stem anthocyanin coloration*.—Absent.
*Length of lateral branch*.—From top to bottom 13 cm.
*Lateral branch color*.—Green 138 A.
*Lateral branch, attachment*.—Weak.
*Branching* (*average number of lateral branches*).—Prolific with 6–8 breaks after pinching.
*Peduncle length*.—3.0–3.5 cm.
*Peduncle color*.—Green 138 A.
*Natural season blooming date*.—5–8 September.

Foliage:
*Color*.—Upper side green 137 A. Under side green 137 C.
*Size*.—Small: length 5 cm. width 4 cm.
*Quantity* (*number per lateral branch*).—12–14.
*Shape*.—Oval.
*Texture upper side*.—Glabrous.
*Texture under side*.—Pubescent.
*Venation arrangement*.—Palmate.
*Shape of the margin*.—Serrated.
*Shape of base of sinus between lateral lobes*.—Round.
*Margin of sinus between lateral lobes*.—Parallel.
*Shape of base*.—Attenuate.
*Apex*.—Mucronate.

Differences with the comparison varieties

| | 'THOR' | 'WARM MEGAN' |
|---|---|---|
| Natural flowering date | September 5–8 | September 26 |
| Flower color | Greyed-orange 169 B | Greyed-orange 171 B |
| Flower size | 6.0–6.5 cm | 5.0–5.5 cm |

I claim:

1. A new and distinct variety of chrysanthemum plant as described and illustrated.

* * * * *